United States Patent [19]

Forestier et al.

[11] Patent Number: 5,178,852

[45] Date of Patent: Jan. 12, 1993

[54] COSMETIC AND PHARMACEUTICAL COMPOSITIONS CONTAINING LIPOPHILIC DERIVATIVES OF BENZYLIDENECAMPHOR AND NEW LIPOPHILIC DERIVATIVES OF BENZYLIDENECAMPHOR

[75] Inventors: Serge Forestier, Claye-Souilly; Alain Lagrange, Chatou; Gerard Lang, Saint-Gratien; Andre Deflandre, Orry-la-Ville; Bernadette Luppi, Sevran, all of France

[73] Assignee: L'Oreal, Paris, France

[21] Appl. No.: 500,940

[22] Filed: Mar. 29, 1990

[30] Foreign Application Priority Data

Mar. 31, 1989 [FR] France .................. 89 04297

[51] Int. Cl.⁵ .................. A61K 7/44; A61K 31/125; A61K 9/48; A61K 9/12
[52] U.S. Cl. .................. 424/60; 424/47; 424/59; 424/71; 424/451; 424/464; 424/401; 514/692; 514/844; 514/887; 514/937; 514/944; 514/962; 514/972
[58] Field of Search ............ 424/47, 59, 60, 45, 424/63, 70, 71, 401, 451, 464; 514/692, 844, 881, 887, 937, 944, 962, 969, 972

[56] References Cited

U.S. PATENT DOCUMENTS

| | | | |
|---|---|---|---|
| 4,290,974 | 9/1981 | Bouillon et al. | 424/40 |
| 4,406,880 | 9/1983 | Bouillon et al. | 424/40 |
| 4,804,542 | 2/1989 | Fischer et al. | 424/456 |
| 4,837,006 | 6/1989 | Rosenbaum et al. | 424/47 |
| 4,952,391 | 8/1990 | Lang et al. | 424/45 |
| 5,004,594 | 4/1991 | Herve et al. | 424/47 |

FOREIGN PATENT DOCUMENTS 2395023 6/1978 France .
2025957 1/1980 United Kingdom ............ 49/743

OTHER PUBLICATIONS

Chemical Abstracts, vol. 112, Reference #185570h (1990) "Preparation of Benzylidene Camphor Derivatives as Sunscreens".
Chemical Abstracts, vol. 105, Reference #18470z (1986) "Antidote for the Phototoxicity of Furocoumarin".

*Primary Examiner*—Thurman K. Page
*Assistant Examiner*—Neil S. Levy
*Attorney, Agent, or Firm*—Jacobson, Price, Holman & Stern

[57] ABSTRACT

The invention relates to cosmetic and pharmaceutical compositions containing the derivatives of benzylidenecamphor of formula:

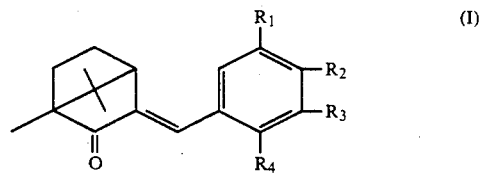

where $R_1$ denotes H, OH, $C_1$–$C_3$ alkyl or $C_1$–$C_8$ alkoxy, $R_3$ denotes OH, $C_1$–$C_3$ alkyl or $C_1$–$C_8$ alkoxy, or else when $R_1$ denotes H or OH, $R_3$ can represent $C_1$–$C_8$ alkyl, $R_2$ and $R_4$ denote H or OH, at least one of the radicals $R_2$ and $R_4$ representing OH.

The compounds (I) are wide-band sunscreens and antioxidants, and are utilized in the treatment of cutaneous inflammations and allergies.

22 Claims, No Drawings

COSMETIC AND PHARMACEUTICAL COMPOSITIONS CONTAINING LIPOPHILIC DERIVATIVES OF BENZYLIDENECAMPHOR AND NEW LIPOPHILIC DERIVATIVES OF BENZYLIDENECAMPHOR

The present invention relates to cosmetic compositions for everyday or antisun use and to pharmaceutical compositions for the treatment of cutaneous inflammations and allergies, containing lipophilic derivatives of benzylidenecamphor, as well as to new lipophilic derivatives of benzylidenecamphor.

It is well known that the skin is sensitive to solar radiation which can cause ordinary sunburn or erythema but also burns which are more or less pronounced.

However, solar radiation likewise has other pernicious effects such as a loss of elasticity of the skin and the appearance of wrinkles leading to premature aging. Even dermatoses can also sometimes be observed.

It is likewise desirable to ensure good protection for the hair against photochemical degradation, in order to prevent a change of shade, a discoloration or a degradation of the mechanical properties.

It is furthermore known that the constituents forming part of cosmetic preparations do not always possess sufficient stability to light and degrade under the action of light radiation.

It is well known that the most dangerous part of the solar radiation is constituted by the ultraviolet radiation of wavelengths less than 400 nm. It is also known that, due to the existence of the ozone layer of the earth's atmosphere, which absorbs part of the solar radiation, the lower limit of ultraviolet radiation reaching the earth's surface is in the neighbourhood of 280 nm.

It consequently appears desirable to have at one's disposal compounds which can absorb ultraviolet radiation within a wide band of wavelengths extending from 280 to 400 nm, that is, both the UV-B rays of wavelengths comprised between 280 and 320 nm and playing a preponderant part in the production of solar erythema, and the UV-A rays of wavelengths comprised between 320 and 400 nm causing tanning of the skin, but also its aging, and facilitating the onset of the erythematous reaction or amplifying this reaction in certain subjects, or even possibly being the cause of phototoxic or photoallergic reactions.

In the course of his research, the Applicant has discovered that the lipophilic derivatives of benzylidenecamphor having the following formula:

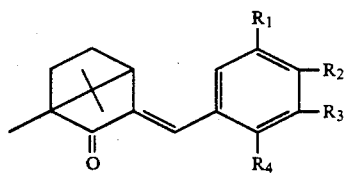

(I)

in which:

$R_1$ represents a hydrogen atom, a hydroxyl radical, a straight-chain or branched-chain $C_1-C_3$ alkyl radical, or a straight-chain or branched-chain $C_1-C_8$ alkoxy radical, $R_3$ represents a hydroxyl radical, a straight-chain or branched-chain $C_1-C_3$ alkyl radical, or a straight-chain or branched-chain $C_1-C_8$ alkoxy radical, or else when $R_1$ represents a hydrogen atom or a hydroxyl radical, $R_3$ can represent a straight-chain or branched-chain $C_1-C_8$ alkyl residue, $R_2$ and $R_4$, identical or different, represent a hydrogen atom or a hydroxyl radical, it being understood that at least one of the radicals $R_2$ and $R_4$ represents a hydroxyl radical, presented, in an unexpected manner, in addition to good screening properties in the wavelength range from 280 to 380 nm, excellent antioxidant properties against the peroxidation of polyunsaturated lipids and likewise against substances capable of undergoing oxidation reactions induced by heat or light (such as proteins, sugars, pigments, vitamins, polymers, etc.).

Now it is known that the peroxidation of lipids implies the formation of intermediate free radicals which damage cell membranes, composed of phospholipids among other materials, and are the cause, particularly, of phenomena of aging of the skin (A.L. TAPPEL in "Federation Proceedings", Vol. 32, No. 8, August 1973).

It is therefore of great interest to have compounds presenting both screening properties in a wide band and antioxidant properties enhancing the screening effect. Such compounds can permit, for example, a better fight against premature aging of the skin due to the peroxidation of cutaneous lipids.

Such compounds can also permit a better preservation of cosmetic or pharmaceutical compositions containing a fatty phase by preventing the development of rancidity of the unsaturated lipids contained therein and which may be of animal origin, such as lanolin, cetin (spermaceti), beeswax, perhydrosqualene, turtle oil, or of vegetable origin such as olive oil, castor oil, maize oil, sweet almond oil, avocado oil, shea oil, sunflower oil, soya oil, groundnut oil, coconut or palm-kernel oils, essential fatty acids such as vitamin F, and certain essential oils present in perfumes, such as lemon or lavender oil.

They can likewise prevent the oxidative degradation of active compounds contained in pharmaceutical compositions (vitamin A, carotenoids, etc.).

The Applicant has likewise discovered, in an extremely surprising manner, that the compounds of formula (I) above can be utilized for the treatment of cutaneous inflammations and allergies.

Apart from their good screening and antioxidant properties, the compounds (I) have an excellent lipophilic character as well as very good thermal and photochemical stability.

These compounds likewise have the advantage of not being toxic or irritant and of being perfectly innocuous to the skin.

They are uniformly distributed in conventional cosmetic vehicles which are able to form a continuous film, and in particular in fatty vehicles, and can thus be applied to the skin to constitute an effective protective film.

Some of the compounds of formula (I) above are new.

They are lipophilic derivatives of benzylidene-camphor of the following formula (I'):

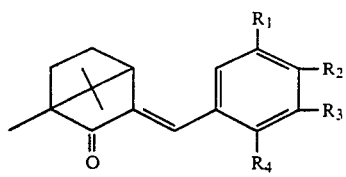

in which $R_1$ to $R_4$ have the meanings indicated for formula (I), provided that when $R_1$ and $R_4$ represent a hydrogen atom and $R_2$ a hydroxyl radical, $R_3$ does not represent an alkoxy radical.

In formula (I'), $R_1$ and $R_3$ can denote, for example, a methyl, ethyl, n-propyl, isopropyl, n-butyl, isobutyl or tert-butyl radical, or else a methoxy, ethoxy, propoxy, butoxy, pentyloxy, hexyloxy, heptyloxy or octyloxy residue.

Among the preferred compounds of formula (I') there can be cited:
3'-tert-butyl-4'-hydroxy-3-benzylidenecamphor,
3',5'-dimethyl-4'-hydroxy-3-benzylidenecamphor,
3',5'-diisopropyl-4'-hydroxy-3-benzylidenecamphor,
3',5,-dimethoxy-4'-hydroxy-3-benzylidenecamphor,
4- 3',4',5'-trihydroxy-3-benzylidenecamphor.

The subject of the present invention is thus the compounds of formula (I') above.

The compounds of formula (I) or (I') are obtained from synthetic camphor (dl-camphor) or from natural camphor (d-camphor) by condensation with an aromatic aldehyde of formula (II) according to the following reaction scheme:

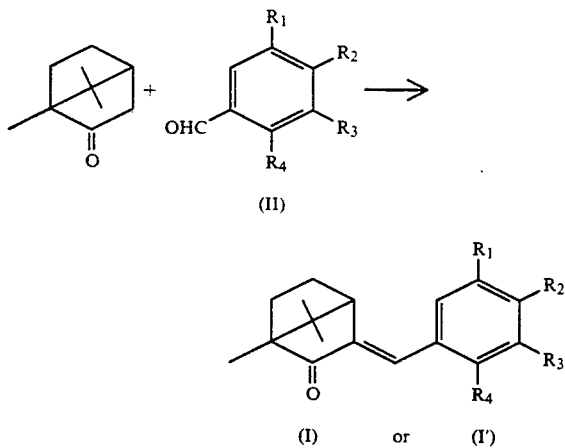

The aldehydes of formula (II) in which the substituents $R_1$ to $R_4$ have the meanings mentioned above for the compounds of formula (I) or (I') are known compounds.

The condensation of the aldehyde (II) with camphor can be carried out in the presence of an alkali metal alcoholate such as sodium methylate or potassium tert-butylate, in a solvent such as toluene, 1,2-dimethoxyethane or 1,2-diethoxyethane, at a temperature comprised between −78° C. and the boiling point of the solvent. The condensation can likewise be carried out in the presence of a mineral base such as an alkali metal amide or hydride, in the presence of a solvent such as 1,2-dimethoxyethane, or an alkali metal hydroxide in toluene or an alcohol, at a temperature comprised between 0° C. and the boiling point of the reaction mixture.

According to a variant, there can be utilized an aldehyde of formula II in which the hydroxyl function(s) is/are blocked by a protective group such as benzyl, trimethylsilyl or tert-butyldimethylsilyl, the condensation with camphor being carried out under the same conditions as above.

According to this variant, the condensation reaction is followed by a hydrogenolysis of the protected derivative, to form the hydroxylated derivative. The hydrogenolysis of the benzyl group can consist either of a catalytic hydrogenation or of a reduction in the presence of a hydrogen-transfer agent, for example, by means of cyclohexene or formic acid, in the presence of a catalyst such as palladium on carbon, and if necessary in the presence of an inert solvent.

The hydrogenolysis of the silylated groups is carried out in a known manner in the presence of fluoride ions.

Another subject of the invention is a cosmetic composition comprising, in a cosmetically acceptable vehicle, an effective amount of at least one derivative of benzylidenecamphor of formula (I') above, as an antioxidant agent and agent screening out UV rays of wavelengths comprised between 280 and 380 nm.

The cosmetic composition of the invention can be utilized as a composition to protect the human epidermis or the hair, or as an antisun composition.

A subject of the present invention is likewise a process for the protection of the skin and of hair, which is natural or has been sensitized, against solar radiation, consisting in applying to the skin or on the hair an effective amount of at least one compound of formula (I') contained in a cosmetically acceptable vehicle.

By "sensitized hair" is to be understood hair which has undergone a permanent waving, dyeing or bleaching treatment.

A subject of the invention is likewise a cosmetic composition, coloured or not coloured, stabilized to light and/or oxidation, and comprising an effective amount of at least one derivative of benzylidenecamphor of formula (I') above.

When it is used as a composition intended to protect the human epidermis against ultraviolet rays or as an antisun composition, the cosmetic composition according to the invention can take the most diverse forms usually utilized for this type of composition. It can in particular take the form of emulsions such as a cream or milk, of oily, alcoholic or aqueous-alcoholic lotions, of oleoalcoholic or aqueous-alcoholic gels, of solid sticks, or can be packaged as an aerosol to form a foam or a spray.

It can contain the cosmetic adjuvants usually used in this type of composition, such as thickeners, emollients, humectants, surface active agents, preservatives, antifoaming agents, perfumes, oils, waxes, lanoline, propellants, colourants and/or pigments having the function of colouring the composition itself or the skin, or any other ingredient usually utilized in cosmetics.

The compound of formula (I') is present in proportions by weight comprised between 0.1 and 4% with respect to the total weight of the cosmetic composition for protecting the human epidermis.

As a solubilizing solvent there can be utilized an oil, a wax, and in general any fat, a mono-hydric alcohol or a lower polyol, or their mixtures. The monohydric alcohols or polyols which are more particularly preferred are ethanol, isopropanol, propylene glycol, glycerin and sorbitol.

One embodiment of the invention is an emulsion in the form of a protective cream or milk, comprising in addition to the compound of formula (I'), fatty alcohols, esters of fatty acids and particularly triglycerides of fatty acids, fatty acids, lanoline, natural or synthetic oils or waxes, and emulsifiers, in the presence of water.

Another embodiment is constituted by oily lotions based on natural or synthetic oils and waxes, lanoline and esters of fatty acids, particularly triglycerides of fatty acids, or by oleoalcoholic or aqueous-alcoholic lotions based on a lower alcohol such as ethanol or on a glycol such as propylene glycol, and/or on a polyol such as glycerin, and water, or else oils, waxes and esters of fatty acids such as triglycerides of fatty acids.

The cosmetic composition of the invention can likewise be an oleoalcoholic or aqueous-alcoholic gel comprising one or more lower alcohols or polyols such as ethanol, propylene glycol or glycerin and a thickener. The oleoalcoholic gels contain a natural or synthetic oil or wax.

The solid sticks are constituted by natural or synthetic waxes and oils, fatty alcohols, esters of fatty acids, lanoline, and other fats.

The present invention likewise relates to antisun cosmetic compositions containing at least one compound of formula (I') and possibly containing other UV-B and/or UV-A screening agents.

In this case, the quantity of screening agent of formula (I') is comprised between 0.2 and 15% by weight, the total quantity of screening agents present in the antisun composition, that is the compound of formula (I') and the other screening agents if required, being comprised between 0.5 and 15% by weight with respect to the total weight of the antisun composition.

When the cosmetic composition according to the invention is intended to protect natural or sensitized hair from UV rays, this composition can take the form of a shampoo, lotion, gel, or emulsion to be rinsed, to be applied before or after shampooing, before or after dyeing or bleaching, before or after permanent-waving, and a styling or treating lotion or gel, a lotion or gel for blow-drying or setting, a hair lacquer, or a composition for permanent waving, dyeing, or bleaching of hair. This composition can contain, apart from the compound of the invention, various adjuvants utilized in this type of composition, such as surface active agents, thickeners, polymers, emollients, preservatives, foam stabilizers, electrolytes, organic solvents, silicone derivatives, oils, waxes, anti-grease agents, colourants and/or pigments having the function of colouring the composition itself or the hair, or any other ingredient usually utilized in hair care.

It contains 0.25 to 4% by weight of the compound of formula (I').

The present invention likewise relates to the cosmetic compositions containing a constituent which is sensitive to light and/or to oxidation and containing at least one compound of formula (I') as a protective agent against ultraviolet rays and as an antioxidant agent. These compositions are constituted by hair-care compositions such as hair lacquers, setting lotions which may be for treatment or disentangling, shampoos, colouring shampoos, hair dyeing compositions, by makeup products such as nail varnishes, creams and oils for treatment of the epidermis, foundations, lipsticks, compositions for skin care such as bath oils or creams, as well as any other cosmetic composition which can present, because of its constituents, problems of stability to light and/or to oxidation during storage.

Such compositions contain 0.1 to 4% by weight of the compound of formula (I').

The invention likewise relates to a process of protection of cosmetic or pharmaceutical compositions against ultra-violet rays and oxidation, consisting in incorporating into these compositions an effective amount of at least one compound of formula (I').

Another subject of the invention is the utilization of the compounds of formula (I') as wide-band sun-screens absorbing in the range of wavelengths from 280 to 380 nm.

A subject of the invention is likewise the application of the compounds of formula (I') as cosmetic products.

Another subject of the invention is the utilization of the compounds of formula (I) as antioxidant agents.

The antioxidant effect of these compounds can be evidenced by chemiluminescence of cell homogenates. This technique is based on the spontaneous emission of light which results from the radiative deactivation of decomposition products of peroxidized lipids. Kinetic study is carried out on ground preparations of rat brain, diluted in a phosphate buffer, and is performed in parallel with a control solution not containing antioxidant and with solutions containing the antioxidant at different concentrations varying from $10^{-7}$ to $10^{-5}$ molar.

By comparison with the control, the concentrations $C_x$ of antioxidant can be determined which result in the inhibition of x% of the peroxidation.

As indicated above, the Applicant has furthermore discovered during his research that the compounds of formula (I) have a pharmacological activity which is of interest in the field of treatment of cutaneous inflammations and allergies.

The subject of the invention is thus the compound of formula (I) for its utilization as a medicament.

A subject of the invention is likewise a pharmaceutical composition containing an effective amount of at least one compound of formula (I) as active ingredient, in a non-toxic vehicle or excipient.

As the preferred compounds (I) there can be cited:
3'-tert-butyl-4'-hydroxy-3-benzylidenecamphor,
3'-methoxy-4'-hydroxy-3-benzylidenecamphor
3'-ethoxy-4'-hydroxy-3-benzylidenecamphor,
3',5'-dimethyl-4'-hydroxy-3-benzylidenecamphor,
3',5'-diisopropyl-4'-hydroxy-3-benzylidenecamphor,
3',5'-dimethoxy-4'-hydroxy-3-benzylidenecamphor,
4',5'-trihydroxy-3-benzylidenecamphor.

The pharmaceutical composition conforming to the invention can be administered orally or applied topically.

For oral administration, the pharmaceutical composition can take the form of tablets, hard gelatin capsules, sugar-coated pills, syrups, suspensions, solutions, emulsions, etc. For topical administration, the pharmaceutical composition according to the invention takes the form of an ointment, cream, pomade, solution, lotion, gel, spray, suspension, etc.

This medicament composition may contain inert or pharmacodynamically active additives, and in particular: moisturizing agents, antibiotics, steroidal or non-steroidal anti-inflammatory agents, carotenoids, or antipsoriasis agents.

This composition can likewise contain agents to improve the flavour, preservatives, stabilizers, moisture regulators, pH regulators, osmotic pressure-modifying agents, emulsifiers, local anesthetics, buffers, etc.

It can also be packaged in delayed or progressive release forms, which are known per se.

The compound of formula (I) conforming to the invention is present in the pharmaceutical compositions in proportions comprised between 0.01 and 80% by weight with respect to the total weight of the composition, and preferably between 0.1 and 20% by weight.

In the therapeutic application, the treatment is determined by the doctor and can vary according to the patient's age, weight and response, as well as the severity of the symptoms.

When the compounds of formula (I) are administered orally, the dosage is generally comprised between 0.1 and 50 mg/kg/day and preferably between 0.2 and 20 mg/kg/day. The duration of the treatment is variable according to the severity of the symptoms and can last between 1 and 25 weeks, in a continuous or discontinuous manner.

The compositions applied topically preferably contain 0.25% to 4% by weight of compound of formula (I).

As a vehicle or excipient for the pharmaceutical composition of the invention, any conventional non-toxic vehicles or excipients may be used.

The following examples are intended to illustrate the invention without, however, having a limiting character.

PREPARATIVE EXAMPLES

Example 1

Preparation of a compound of general formula (I' in which $R_1 = R = H$, $R_2 = OH$, $R_3 = $ tert-butyl:

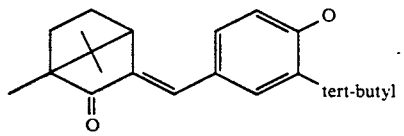

(a) Preparation of 4'-benzyloxy-3'-tert-butyl-3-benzylidene camphor 3 g (0.02 mol) of dl-camphor and 1.1 g (0.02 mol) of sodium methylate are heated under reflux for 15 minutes in 30 cm³ of 1,2-dimethoxyethane. A solution of 5.4 g (0.02 mol) of 4-benzyloxy-3-tert-butyl benzaldehyde in 20 cm³ of 1,2-dimethoxyethane is added to the hot mixture and kept under reflux for 4 hours.

The reaction mixture is cooled to ambient temperature, then poured into an aqueous solution of sodium chloride acidified with hydrochloric acid. Extraction with dichloromethane is performed. The solvent is distilled off under reduced pressure and the residue is recrystallized from a minimum quantity of cyclohexane.

The expected product is obtained in the form of white crystals with a yield of 45%.

(b) Preparation of 3'-tert-butyl-4'-hydroxy-3-benzylidene camphor 3.2 g (0.008 mol) of 4'-benzyloxy-3'-tert-butyl-3-benzylidenecamphor obtained above and 2 g of palladium-on-charcoal containing 50% of water (5% by weight of palladium with respect to the charcoal) in 40 cm³ of formic acid are agitated under argon for 2 hours 30 minutes at ambient temperature, then for 1 hour on a boiling water bath. Cooling is followed by dilution with 20 cm³ of water and filtration on celite. The filter cake is washed with dichloromethane, then with water. The organic phase is washed with water, then evaporated to dryness. The residue is recrystallized from diisopropyl ether.

1 g of the expected product is obtained in the form of white crystals possessing the following properties:
Melting point: 216° C.,
Elemental analysis $C_{21}H_{28}O_2$.

|  | C % | H % | O % |
|---|---|---|---|
| Calculated | 80.73 | 9.03 | 10.24 |
| Found | 80.71 | 9.10 | 10.37 |

UV spectrum ($CH_2Cl_2$):
$\lambda_{max}$:316 nm,
$\epsilon_{max}$:23700.

Example 2

Preparation of a compound of general formula (I) in which $R_1 = R_4 = H$, $R_2 = OH$, $R_3 = OCH_3$:

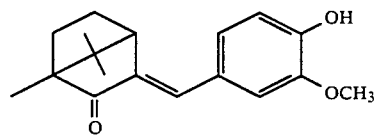

192 g (1.26 mol) of dl-camphor are dissolved in 1 litre of dry 1,2-dimethoxyethane. Under nitrogen, 120 g (2.52 mol) of sodium hydride are added as a 50% suspension in oil, previously washed with dry hexane. The mixture is brought to 80° C. during 1 hour 30 minutes, and a solution of 183 g (1.2 mol) of vanillin in 350 cm³ of dry 1,2-dimethoxyethane is then added dropwise during 1 hour 30 minutes. The reaction mixture is heated under reflux for 10 hours. After cooling, it is poured slowly onto 3 kg of ice. Acidification with 6N hydrochloric acid is followed by extraction with dichloromethane. The organic phase is dried over sodium sulfate. The solvent is distilled off under reduced pressure. The product is recrystallized twice from diisopropyl ether.

150 g of the expected product are obtained in the form of white crystals having the following properties:
Melting point: 118° C.,
Elemental analysis: $C_{18}H_{22}O_3$:

|  | C % | H % |
|---|---|---|
| Calculated | 75.49 | 7.74 |
| Found | 75.56 | 7.73 |

UV spectrum (ethanol):
$\lambda_{max}$:334 nm,
$\epsilon_{max}$:19600.

Example 3

Preparation of a compound of general formula (I) in which $R_1 = R_4 = H$, $R_2 = OH$, $R_3 = OC_2H_5$

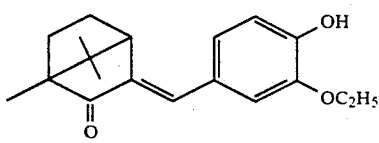

This compound is obtained according to the procedure described in Example 2 above, in which the vanillin is replaced by ethylvanillin.

The product obtained has the following properties:
Melting point: 100° C.,
Elemental analysis: $C_{19}H_{24}O_3$:

|  | C % | H % | O % |
| --- | --- | --- | --- |
| Calculated | 75.97 | 8.05 | 15.98 |
| Found | 76.10 | 8.10 | 16.22 |

UV spectrum (methanol):
$\lambda_{max}$:335 nm,
$\epsilon_{max}$:19500.

Example 4

Preparation of a compound of general formula (I') in which $R_1=R_3=CH_3$, $R_2=OH$, $R_4=H$

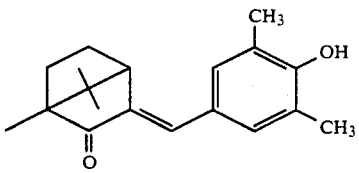

This compound is obtained according to the procedure described in Example 2 above, in which the vanillin is replaced by 3',5'-dimethyl-4'-hydroxybenzaldehyde and the sodium hydride by the equivalent quantity of potassium tert-butylate.

The product obtained has the following proper Melting
Melting point: 170° C.,
Elemental analysis: $C_{19}H_{24}O_2$:

|  | C % | H % | O % |
| --- | --- | --- | --- |
| Calculated | 80.24 | 8.51 | 11.25 |
| Found | 80.21 | 8.50 | 11.28 |

UV spectrum ($CH_2CL_2$):
$\lambda_{max}$:318 nm,
$\epsilon_{max}$:24100.

Example 5

Preparation of a compound of general formula (I') in which $R_1=R_3=OCH_3$, $R_2=OH$, $R_4=H$

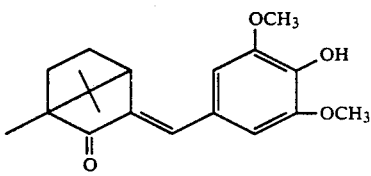

This compound is obtained by the procedure described in Example 2 above, in which the vanillin is replaced by 3',5'-dimethoxy-4'-hydroxybenzaldehy,ie and the sodium hydride is replaced by the equivalent quantity of potassium tert-butylate.

The product obtained has the following properties:
Melting point: 158° C.,
Elemental analysis: $C_{19}H_{24}O_4$:

|  | C % | H % | O % |
| --- | --- | --- | --- |
| Calculated | 72.13 | 7.65 | 20.23 |
| Found | 72.17 | 7.64 | 20.30 |

UV spectrum (dichloromethane):
$\lambda_{max}$:327 nm,
$\epsilon_{max}$:21300.

Example 6

Preparation of a compound of general formula (I') in which $R_1=R_3=$isopropyl, $R_2=OH$, $R_4=H$:

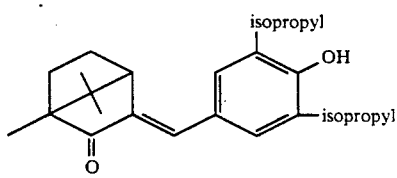

This compound is obtained according to the procedure described in Example 2 above, in which the vanillin is replaced by 3',5'-diisopropyl-4'-hydroxybenzaldehyde and the sodium hydride is replaced by the equivalent quantity of potassium tert-butylate.

The product obtained has the following properties:
Melting point: 159°-160° C.,
Elemental analysis $C_{23}H_{32}O_2$:

|  | C % | H % | O % |
| --- | --- | --- | --- |
| Calculated | 81.13 | 9.47 | 9.40 |
| Found | 81.08 | 9.41 | 9.66 |

UV spectrum ($CH_2Cl_2$):
$\lambda_{max}$:318 nm,
$\epsilon_{max}$:25300.

Demonstration of antioxidant properties by chemiluminescence of cell homocenates The test of chemiluminescence is carried out according to the publication of E.A. LISSI, T. CACERES and L.A. VIDELA, "Visible Chemiluminescence from rat brain homogenates undergoing autoxidation. I. Effect of additives and products accumulation" in "Journal of Free Radicals in Biology and Medicine", Vol. 2, pp. 63-69 (1986). This test was simplified in that only the chemiluminescence was measured, without measuring the accumulation of thiobarbituric acid after 1 hour of irradiation. However, according to the publication, there is a good correlation between the chemiluminescence and the measurement of the accumulation of thiobarbituric acid.

Rat brains are taken immediately after dislocation of the cervical vertebrae. They are washed with a buffer solution containing 140 mM of NaCl and 40 mM of potassium phosphate, freed of visible blood vessels and of the external membrane, then ground with 4 times their volume of buffer solution. This ground preparation is diluted 3 times with the buffer solution (total dilution 12 times with respect to the starting organs).

10 ml of diluted homogenate is introduced into counting vials containing 200 μl of solution of the antioxidant product to be tested, dissolved at different concentrations in methanol or dimethyl sulphoxide. Immediately after agitation, the vials are introduced into a scintillation counter (BECKMAN) and periodically counted.

A study is made in parallel on a control solution containing no antioxidant.

A curve of chemiluminescence intensity as a function of time is thus established for each concentration.

By comparison of the slopes of the curves obtained with the solutions at different concentrations and with the control solution, $C_{50}$ is determined, that is, the concentration of antioxidant resulting in the inhibition of 50% of the peroxidation.

Compound of Example 1: $C_{50} = 2.70 \times 10^{-6} M$
Compound of Example 2: $C_{50} = 1.22 \times 10^{-6} M$
Compound of Example 3: $C_{50} = 1.10 \times 10^{-6} M$
Compound of Example 4: $C_{50} = 0.70 \times 10^{-6} M$
Compound of Example 5: $C_{50} = 0.35 \times 10^{-6} M$
Compound of Example 6: $C_{50} = 0.90 \times 10^{-6} M$ Tested under the same conditions, di-tert-butyl-hydroxytoluene (BHT), which is a conventional antioxidant, has a $C_{50}$ of $3.20 \times 10^{-6} M$.

EXAMPLES OF APPLICATION

Example A

Skin protecting gel

| | |
|---|---|
| Compound of Example 1 | 0.12 g |
| Glycerin | 12.0 g |
| Polyacrylic acid crosslinked by a polyfunctional agent sold under the trademark "CARBOPOL 934" by GOODRICH | 0.8 g |
| Ethanol | 15.0 g |
| Preservative | 0.2 g |
| Perfume | 0.2 g |
| Triethanolamine | qs pH 5.3 |
| Demineralized water | qsp 100 g |

The composition of Example 1 is dissolved in the ethanol-glycerin mixture; water, the preservative and the perfume are added. The Carbopol is homogeneously dispersed in this aqueous phase, and the pH is adjusted to 5.3 pl with triethanolamine.

Example B

Antisum oil

The following ingredients are mixed, with heating to 40°-45° C. if required to homogenize them:

| | |
|---|---|
| Compound of Example 2 | 0.6 g |
| Benzoate of $C_{12}$-$C_{15}$ alcohols sold under the trademark "FINSOLV TN" (FINETEX) | 30.0 g |
| Refined, stabilized sunflower oil | 20.0 g |
| Perfume | 1.0 g |
| Cyclic dimethyl polysiloxane sold under the trademark "VOLATILE SILICONE 7207" (UNION CARBIDE) | qsp 100 g |

Example C

Antisum milk

| | |
|---|---|
| Compound of Example 6 | 0.25 g |
| Benzylidene camphor | 2.0 g |
| Mixture of fatty acids, polyglycerolated esters, and silicone surface active agents "ABIL WS08" (GOLDSCHMIDT) | 5.0 g |
| White vaseline | 2.0 g |
| Beeswax | 2.5 g |
| Benzoate of $C_{12}$-$C_{15}$ alcohols "FINSOLV TN" (FINETEX) | 19.0 g |
| Glycerin | 5.0 g |
| Sodium chloride | 2.0 g |
| Perfume | 0.4 g |
| Preservative | 0.2 g |
| Demineralized water | qsp 100 g |

The compound of Example 6 and the benzylidene-camphor are dissolved in the fats and in the emuslifier and are heated to 70°-80° C.; the aqueous phase, constituted by the water, the sodium chloride and the glycerin, is heated to the same temperature; the aqueous phase is added to the fatty phase, under vigorous agitation, cooling is then allowed under moderate agitation, and at about 40° C. the perfume and preservative are added. A water-in-oil emulsion is obtained.

Example D

Antisum milk

| | |
|---|---|
| Compound of Example 1 | 1.5 g |
| 2-Ethylhexyl p-methoxycinnamate "PARSOL MCX" (GIVAUDAN) | 3.5 g |
| 2-Hydroxy-4-methoxybenzophenone "UVINUL M40" | 1.0 g |
| Cetyl alcohol | 1.0 g |
| Oleocetyl alcohol with 30 mols of ethylene oxide "MERGITAL OC 30" (HENKEL) | 5.0 g |
| Stearyl alcohol | 4.0 g |
| Synthetic oil of formula: | 2.0 g |

$$C_{15}H_{31}COOCH_2-\underset{\underset{OH}{|}}{CH}-CH_2OCH_2-\underset{\underset{C_2H_5}{|}}{CH}-C_4H_9$$

| | |
|---|---|
| 90:10 mixture of cetyl/stearyl 2 ethyl-hexanoate and isopropyl myristate "CERAMOLL" (Creations Aromatiques) | 2.0 g |
| Liquid paraffin | 8.0 g |
| Propylene glycol | 4.0 g |
| Preservative | 0.2 g |
| Perfume | 0.4 g |
| Demineralized water | qsp 100 g |

This relates to an oil-in-water emulsion. The compound of Example 1 and the screening agents are dissolved in the fats at about 70°-80° C.; the aqueous phase containing the water, propylene glycol and emulsifier is heated tothe same temperature, and the fatty phase is added to the aqueous phase under vigorous agitation; cooling is then allowed under moderate agitation, and the preservative and perfume are added at about 40° C.

Example E

Antisum stick

The following solid stick is prepared:

| | |
|---|---|
| Compound of Example 4 | 1.0 g |
| Ozokerite wax "SP10205" (STRAHL ET PITSCH) | 20.0 g |
| Beeswax | 7.0 g |

| -continued | |
|---|---|
| Oleyl alcohol | 12.0 g |
| Hydrogenated lanolin "HYDROLAN H" (ONYX CHEMICAL) | 8.0 g |
| Lanolin oil "ARGONOL 60" (WESTBROOK LANOLIN) | 8.0 g |
| Carnauba wax | 1.0 g |
| Benzoate of $C_{12}$-$C_{15}$ alcohols "FINSOLV TN" (FINETEX) | 17.0 g |
| Octamethylcyclotetrasiloxane "ABIL K4" (GOLDSCHMIDT) | 3.0 g |
| Liquid paraffin | qsp 100 g |

The various components are melted at about 70°–75° C. so as to obtain a liquid phase in which the compound of Example 4 is then dissolved. This solution is run into moulds and allowed to cool.

Example F

Antisum cream

The following cream is prepared in the same manner as in Example D and constitutes an oil-in-water emulsion, the aqueous phase of which is constituted by water, sorbitol, sodium lactate and the emulsifier and in which is dissolved 4-[(2-oxo-3-bornylidene)methyl]henyl-trimethylammonium methylsulfate:

| Compound of Example 5 | 0.5 g |
|---|---|
| 4-[(2-oxo-3-bornylidene)methyl]phenyl-trimethylammonium methylsulfate | 4.0 g |
| 60% sodium lactate | 1.0 g |
| Mixture of cetyl/stearyl alcohol and oxyethylenated cetyl/stearyl alcohol with 33 mols of ethylene oxide "SINNOWAX AO" (HENKEL) | 7.5 g |
| Non-autoemulsifiable mixture of glycerol mono- and di-stearate | 2.1 g |
| Cetyl alcohol | 1.0 g |
| Myristyl alcohol "SIPOL C14" (HENKEL) | 0.6 g |
| 70% sorbitol | 3.0 g |
| Isopropyl palmitate | 10.0 g |
| Liquid paraffin | 7.0 g |
| Preservative | 0.2 g |
| Perfume | 0.6 g |
| Demineralized water | qsp 100 g |

Pharmaceutical compositions utilized in topical administration:

Example G

Soothing ointment (To be applied to irritated skin, to soothe it)

| Compound of Example 1 | 2.0 g |
|---|---|
| Light liquid paraffin | 9.1 g |
| Silica sold by DEGUSSA under the name "AEROSIL 200" | 9.2 g |
| Isopropyl myristate | qsp 100 g |

Example H

Anti-inflammatory cream (oil-in-water)

| Compound of Example 1 | 3.0 g |
|---|---|
| Sodium dodecyl sulphate | 0.8 g |
| Glycerol | 2.0 g |
| Stearyl alcohol | 20.0 g |
| Triglycerides of capric/caprylic acids sold by DYNAMIT NOBEL under the name of "MIGLYOL 812" | 20.0 g |
| Preservatives | qs |
| Demineralized water | qsp 100 g |

Example I

Soothing gel

| Compound of Example 5 | 1.0 g |
|---|---|
| Hydroxypropyl cellulose sold by HERCULES under the name of "KLUCEL HF" | 2.0 g |
| Ethanol | 70.0 g |
| Water | qsp 100 g |

We claim:

1. A derivative of benzylidenecamphor that has formula (I'):

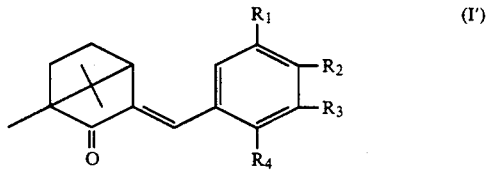

wherein :
R$_1$ is selected from the group consisting of hydrogen atoms, hydroxyl radicals, straight-chain or branched-chain $C_1$-$C_3$ alkyl radicals and straight-chain or branched-chain $C_1$-$C_8$ alkoxy radicals;

R$_3$ is selected from the group consisting of hydroxyl radicals, straight-chain or branched-chain $C_1$-$C_3$ alkyl radicals and straight-chain or branched-chain $C_1$-$C_8$ alkoxy radicals, or if R$'_1$ is a hydrogen atom or a hydroxyl radical, then R$_3$ is selected from the group consisting of hydroxyl radicals, straight-chain or branched-chain $C_1$-$C_8$ alkoxy radicals and straight-chain or branched-chain $C_1$-$C_8$ alkyl radicals;

R$_2$ and R$_4$, which may be identical or different, are hydrogen atoms or hydroxyl radicals, as long as at least one of R$_2$ and R$_4$ is a hydroxyl radical;

with the proviso that when R$_1$ and R$_4$ are hydrogen atoms and R$_2$ is a hydroxyl radical, then R$_3$ is not an alkoxy radical.

2. A benzylidenecamphor derivative of claim 1 selected from the group consisting of 3'-tert-butyl-4'-hydroxy-3-benzylidenecamphor, 3',5'-dimethyl-4'-hydroxy-3-benzylidenecamphor, 3',5'-diiso-propyl -4'-hydroxy-3-benzylidenecamphor, 3',5'-dimethyxy-4'-hydroxy -3-benzylidenecamphor, and 3',4', 5'-trihydroxy-3-benzyli-denecamphor.

3. A cosmetic composition, comprising, in a cosmetically acceptable vehicle, an effective antioxidizing and sunscreening concentration of at least one benzylidenecamphor derivative of claim 1,
wherein said concentration is effective for inhibiting the peroxidation of polyunsaturated lipids and heat or light induced oxidation reactions and for screening out UV rays of wavelengths between 280 and 380 nm.

4. The cosmetic composition of claim 3, wherein at least one of said benzylidenecamphor derivatives is selected from the group consisting of 3'-tert-butyl-4'-hydroxy-3-benzylidenecamphor, 3',5'-dimethyl-4'-hydroxy-3-benzylidenecamphor, 3',5'-diiso-propyl -4'hydroxy-3-benzylidenecamphor,3', 5'-dimethoxy-4'-hydroxy-3-benzylidenecamphor, and 3', 4',5'-trihydroxy-3-benzylidenecamphor.

5. The cosmetic composition of claim 3 whihc is formulated as an emulsion, a lotion, an oleoalcoholic or aqueous-alcoholic gel, a solid stick, or an aerosol.

6. The cosmetic composition of claim 5, further comprising at least one cosmetic adjuvant that is selected from the group consisting of thickeners, emollients, humectants, surface acitve agents, preservatives, antifoaming agents, perfumes, oils, waxes, lanoline, lower monohydric alcohols and polyols, propellants, colorants and pigments.

7. The cosmetic composition of claim 5 wherein said effective concentration of said derivative is 0.1 to 4% by weight.

8. The cosmetic composition of claim 5, which is formulated as an antisum composition, wherein said effective concentration of said derivative is 0.2 to 15% by weight.

9. The antisun composition of claim 8, further comprising an additional sunscreening compound, other than a derivative of formula (I'), that screens out UV-B or UV-A rays.

10. The cosmetic composition of claim 3 that is formulated for application to the hair, wherein said formulation is a shampoo, lotion, gel, or emulsion to be rinsed, styling or treating lotion or gel, lotion or gel for blow-drying or setting, hair lacquer, or a composition for permanent waving, bleaching or dyeing, and said effective concentration of said derivative is 0.25 to 4% by weight.

11. The cosmetic composition of claim 3 that is a light and oxidation stable composition, which is colored or not colored, and is formulated as a hair-care composition, a makeup product, or a composition for care or treatment of the skin, wherein said effective concentration of said derivative is 0.1 to 4% by weight.

12. A process for the protection of the skin and of hair, which is natural or has been sensitized against ultraviolet radiation, comprising applying to the skin or a on the hair an effective amount of the cosmetic composition of claim 3.

13. A method for protecting a cosmetic or pharmaceutical composition against ultraviolet (UV) rays and oxidation, comprising incorporating into said composition an effective concentration of at least one benzylidenecamphor derivatie of claim 1, wherein said concentration is sufficient to protect said composition against the damaging effects of UV rays and oxidation.

14. In a process for treating a subject afflicted with a cutaneous inflammation or an allergy by administering to the subject an effective amount of a pharmaceutically-active ingredient, the improvement wherein the active ingredient is a derivative of benzylidenecamphor that has formula (I):

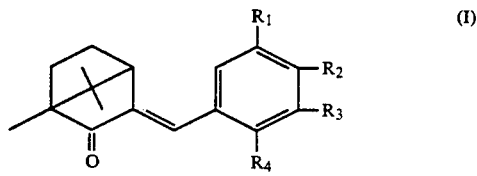

wherein:
$R_1$ is selected from the group consisting of hydrogen atoms, hydroxyl radicals, straight-chain or branched-chain $C_1-C_3$ alkyl radicals and straight-chain or branched-chain $C_1-C_8$ alkoxy radicals;

$R_3$ is selected from the group consisting of hydroxyl radicals, straight-chain or branched-chain $C_1-C_3$ alkyl radicals and straight-chain or branched-chain $C_1-C_8$ alkoxy radicals, or if $R_1$ is a hydrogen atom or a hydroxyl radical, then $R_3$ is selected from the group consisting of hydroxyl radicals, straight-chain or branched-chain $C_1-C_8$ alkoxy radicals and straight-chain or branched-chain $C_1-C_8$ alkyl radicals;

$R_2$ and $R_4$, which may be identical or different, are hydrogen atoms or hydroxyl radicals, as long as at least one of $R_2$ and $R_4$ is a hydroxyl radical.

15. A process of claim 14 wherein the benzylidenecamphor derivative is a member selected from the group consisting of 3'-tert-butyl-4'-hydroxy-3-benzylidene camphor, 3'-methoxy-4'-hydroxy-3-benzylidene camphor, 3'-ethoxy-4'-hydroxy -3-benzylidene camphro, 3',5'-dimethyl-4'-hydroxy-3-benzylidene camphor, 3',5'-diisopropyl-4'-hydroxy-3-benzylidene camphor, 3'5'-dimethoxy-4'-hydroxy-3-benzylidene camphor, and 3',4',5'-trihydroxy-3-benzylidene camphor.

16. A process of claim 14 for the treatment of cutaneous inflammations and allergies, which comprises administering orally to the patient a dosage form 0.1. to 50 mg/kg/day of a compound of formula (I) for to 25 weeks.

17. A pharmaceutical composition, comprising an effective concentration of at least one benzylidenecamphor derivative in a pharmaceutically acceptable non-toxic vehicle or excipient, wherein said concentration is effective for the treatment of cutaneous inflammations and allergies and the derivative is a compound of formula (I):

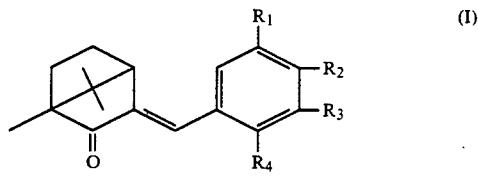

wherein:
$R_1$ is a member selected from the group consisting of hydrogen atoms, hydroxyl radicals, straight-chain or branched-chain $C_1-C_3$ alkyl radicals and straight-chain or branched-chain $C_1-C_8$ alkoxy radicals;

$R_3$ is a member selected from the group consisting of hydroxyl radicals, straight-chain or branched-chain $C_1-C_3$ alkyl radicals and straight-chain or branched-chain $C_1-C_8$ alkoxy radicals; or, if $R_1$ is a hydrogen atom or a hydroxyl radical, then $R_3$ is a member selected from the group consisting of hydroxyl radicals, straight-chain or branched-chain $C_1-C_8$ alkoxy radicals and straight-chain or branched-chain $C_1-C_8$ alkyl radicals;

$R_2$ and $R_4$, which may be identical or different, are hydrogen atoms or hydroxyl radicals, as long as at least one of $R_2$ and $R_4$ is a hydroxyl radical.

18. The pharmaceutical composition of claim 17 formulated for topical application, wherein said formulation is a cream, ointment, pomade, solution, gel, lotion, spray or suspension.

19. The pharmaceutical composition of claim 17 formulated for oral administration, wherein said formulation is tablets, hard gelatin capsules, sugar-coated pills, syrups, suspensions, solutions or emulsions.

20. The pharmaceutical composition of claim 18, wherein said effective concentration is between 0.25 and 4% by weight with respect to the total weight of the composition.

21. A process for the treatment of cutaneous inflammations and allergies, comprising topically applying an effective amount of the composition of claim 20 to the patient.

22. A benzylidenecamphor derivative that is a member selected from the group consisting of 3'-tert-butyl-4'-hydroxy-3-benzylidene camphor, 3'5'-dimethyl-4'-hydroxy-3-benzylidene camphor, 3'5'-diisopropyl-4'-hydroxy-3-benzylidene camphor, 3'5'-dimethoxy-4'-hydroxy-3-benzylidene camphor, and 3',4',5'-trihydroxy-3-benzylidene camphor.

* * * * *